United States Patent [19]

Wiest et al.

[11] Patent Number: 5,098,387

[45] Date of Patent: Mar. 24, 1992

[54] DEVICE FOR IRRIGATION OF AND ASPIRATION FROM BODY CAVITIES

[75] Inventors: Peter P. Wiest, Hessenalle 8, D-1000 Berlin 19; Hubert G. Fuchs, Berlin, both of Fed. Rep. of Germany

[73] Assignee: Peter P. Wiest, Berlin, Fed. Rep. of Germany

[21] Appl. No.: 593,082

[22] Filed: Oct. 5, 1990

[30] Foreign Application Priority Data

Oct. 9, 1989 [DE] Fed. Rep. of Germany ....... 3933856

[51] Int. Cl.5 ............................................. A61M 5/00
[52] U.S. Cl. ..................................... 604/153; 604/31; 604/67; 604/131; 417/475
[58] Field of Search ................. 604/131, 151, 153, 30, 604/31, 65, 66, 67, 118, 119, 120; 128/DIG. 12, DIG. 13; 417/477, 475

[56] References Cited

U.S. PATENT DOCUMENTS

| | | | |
|---|---|---|---|
| 3,920,014 | 11/1975 | Banko | 604/118 |
| 4,180,074 | 12/1979 | Murry et al. | 604/31 |
| 4,231,366 | 11/1980 | Schael | 604/67 |
| 4,299,221 | 11/1981 | Phillips et al. | 604/119 |
| 4,526,573 | 7/1985 | Lester et al. | 604/119 |
| 4,705,500 | 11/1987 | Reimels et al. | 604/30 |
| 4,715,435 | 12/1987 | Foret | 417/475 |
| 4,755,168 | 7/1988 | Romanelli et al. | 604/31 |
| 4,769,001 | 9/1988 | Prince | 604/67 |
| 4,820,265 | 4/1989 | Desatnick et al. | 604/65 |
| 4,856,972 | 8/1989 | Van Benschoten et al. | 604/153 |
| 4,886,431 | 12/1989 | Soderquist et al. | 417/477 |
| 4,935,005 | 6/1990 | Haines | 604/30 |

FOREIGN PATENT DOCUMENTS

| | | |
|---|---|---|
| 3036076 | 4/1981 | Fed. Rep. of Germany . |
| 3309918 | 10/1983 | Fed. Rep. of Germany . |
| 8302264 | 1/1985 | Netherlands ............ 604/131 |
| WO87/00759 | 2/1987 | World Int. Prop. O: . |

Primary Examiner—Gene Mancene
Assistant Examiner—Michael Lynch
Attorney, Agent, or Firm—McGlew & Tuttle

[57] ABSTRACT

The present invention pertains to a device for irrigation of and aspiration from body cavities, especially during surgical laparoscopy, comprising a delivery pump and a suction pump and tubing lines, which are connected to these and lead to the body cavity. A device for irrigation of and aspiration from body cavities, which can be operated in a very simple manner and fully meets sterility requirements is provided. The suction pressure and the irrigation pressure can be finely controlled in a simple manner, a control device 1 for alternate irrigation of and aspiration from the body cavity is provided according to the present invention; the control device 1 is connected to a control line 3 and to a control valve 20 arranged in its path and controls the delivery and suction pumps 13 and 14 as a function of this control line, and the setting of the gas ballast in the control line 3 by means of the control valve 20 brings about control of the pressure and/or rotation speed of the delivery and suction pumps 13 and 14 (FIG. 2).

13 Claims, 3 Drawing Sheets

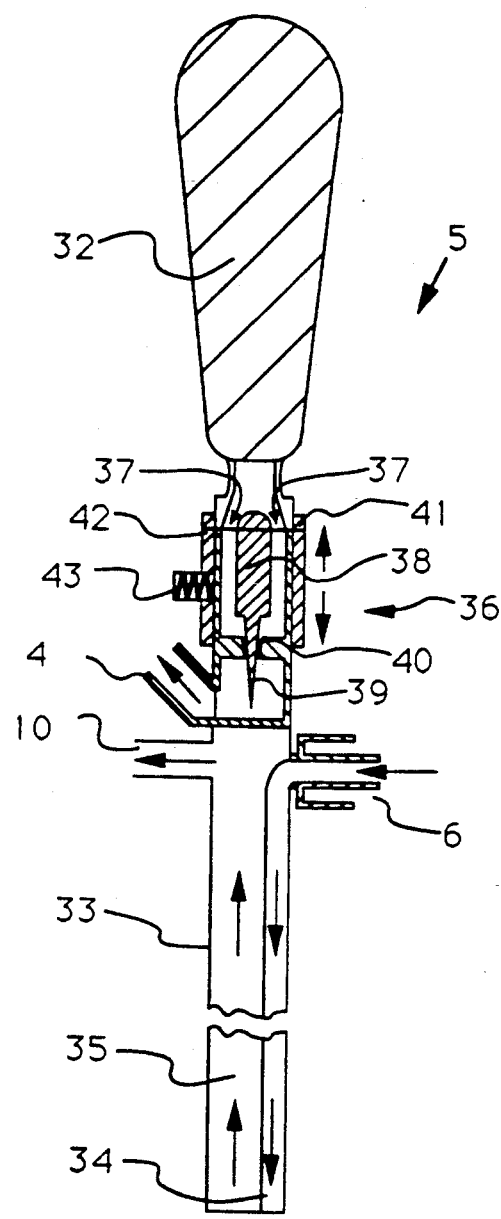
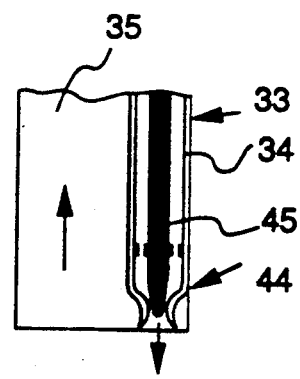
*Fig.3*  *Fig.4*

DEVICE FOR IRRIGATION OF AND ASPIRATION FROM BODY CAVITIES

FIELD OF THE INVENTION

The present invention pertains to a device for irrigation of and aspiration from body cavities, especially during surgical laparoscopy, comprising a delivery pump and a suction pump, as well as tubing lines connected to these and leading to the body cavity.

BACKGROUND OF THE INVENTION

In a prior-art device of this type, the irrigation fluid is supplied via a disposable irrigation water bottle made from glass. The pressure needed for irrigation is generated by means of an outflow spike introduced deep down and by means of compressed air pressed in from the top. The irrigation is initiated by a valve on the device. A collecting bottle, which is evacuated by a pump suitable for gases only, is used for aspiration. Aspiration is also initiated at a valve provided on the device.

The poor controllability of aspiration, solely by selecting the position of the suction valves on the device, is disadvantageous. A minimally opened suction valve can soon become plugged with aspirated blood clots. In addition, the collecting bottle must be emptied frequently. If emptying is not performed due to negligence and the like, and if the overflow safety unit is stuck, secretion will be drawn into the vacuum suction pump, which thus becomes unfit for use.

Furthermore, the handling of the irrigation bottle is very cumbersome and time-consuming. To operate it, a thick spike must be inserted to remove the fluid and a second spike must be inserted to generate pressure. In addition, hygienic problems arise due to both unfiltered air being pumped into the bottle and the difficulty of handling the very large puncturing spike. In addition, the shape and intensity of the stream of irrigation fluid can be altered only slightly. Finally, the user is forced to use the irrigation fluid bottle supplied.

SUMMARY AND OBJECTS OF THE INVENTION

It is an object of the present invention to provide a device of the type described above for the irrigation of and aspiration from body cavities, which can be operated in a very simple manner, which fully meets sterility requirements, and in which both the aspiration pressure and the irrigation pressure can be finely controlled in a simple manner.

The device according to the present invention for irrigation from and aspiration from body cavities comprises a control device for a delivery pump and a suction pump, as well as a control valve for controlling the pressure and/or the rotation speed of the delivery pump and the suction pump. This permits the fine control of both the suction pressure and the irrigation pressure in a simple manner, so that the device according to the present invention can be operated in a very simple manner.

According to a preferred embodiment of the invention, the control valve is arranged in the area of the handle of a medical instrument provided with a hollow shaft. The tubing lines connected to the delivery pump and the suction pump can be connected to two connection ports of the medical instrument, Thus, the control valve is regularly in the operator's action zone, and he or she is able to operate the delivery pump and the suction pump from the instrument and thus accurately control both the irrigation and the aspiration. For high safety, the control device is provided with a vacuum pump, which draws air through the control valve via a tubing line.

In another preferred embodiment of the present invention, the medical instrument has two lumina, and the irrigation tube, which has a smaller diameter, is arranged inside the suction tube, which has a larger diameter. The control valve is arranged in the handle of the medical instrument and can be set to various, different nozzle openings for a needle valve by means of a locking device. Another needle valve, whose valve needle is adjustable to form different valve openings, is arranged at the outlet of the irrigation tube inside the medical instrument.

In another, particularly advantageous embodiment of the present invention, the delivery pump and the suction pump are formed by two peristaltic/roller pumps which can be switched over alternatingly for irrigation and aspiration and can be driven by a common drive motor by means of a switching gear. The two pump rollers are mounted on shafts of the switching gear that are arranged coaxially in each other. The two peristaltic pumps have a common pressing bar. Thus, two peristaltic pumps, which are driven mutually for irrigation and aspiration by means of the switching gear and a common motor, are used for irrigation and aspiration. The coaxial arrangement of the two rollers is highly advantageous.

This makes it possible to integrate the two pump tubings in a common holder, which is designed in a form-fit manner with the pump combination and prevents insertion in an incorrect position. In addition, a pressing bar presses both tubings against the respective rollers, as a result of which handling is greatly simplified.

The device according to the present invention is used especially in surgical laparoscopy, specifically for irrigation of tissues covered with blood clots. Furthermore, the device is used for rinsing off and separating mist-like and vapor-like residues in the abdominal gas bubble during or after the use of a surgical laser and for drawing up body fluids and the irrigation medium.

It is a further object of the invention to provide a surgical aspiration and irrigation device which is simple in design dependable in operation and cost effective to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a cross sectional schematic view of a medical instrument connected to the device, with a connection for the control device according to the invention;

FIG. 4 is a sectional view of the distal end of a modified embodiment of the medical instrument on a larger scale;

DETAILED DESCRIPTION OF THE PREFERRED EMBODIMENT

Figure 1:
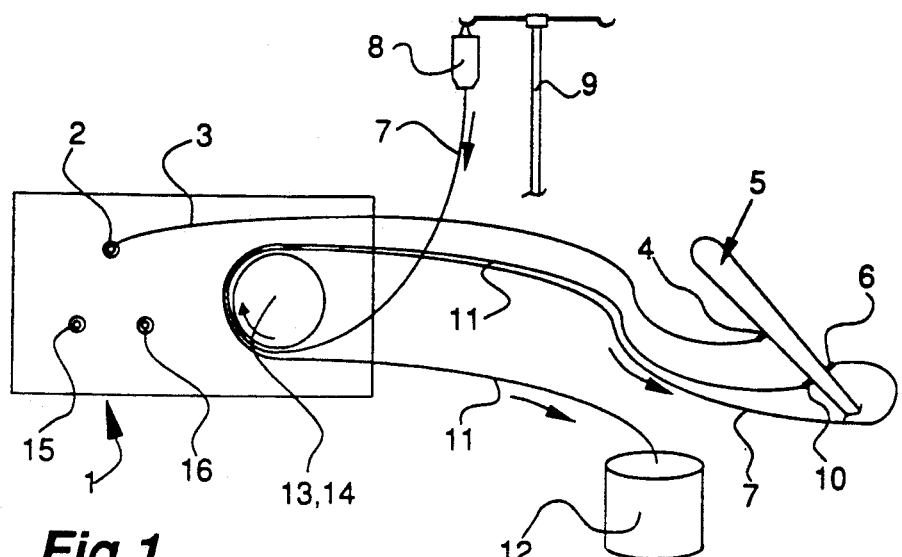
FIG. 1 is a schematic representation of the system and device arrangement according to the invention.

Referring to the drawings and in particular to FIG. 1, the invention comprises a control unit 1 accommodated in a housing, with a connection 2 for a control line 3. The control line 3 is led to a connection port 4 on a medical instrument 5. An irrigation line 7, which is led to an irrigation fluid supply reservoir 8 suspended on a stand 9, is connected to another connection port. An aspiration line 11, which is led to a collection reservoir 12, is connected to another connection port 10 of the medical instrument 5. The irrigation line 7 and the aspiration line 11 are led around delivery and suction pumps designed as roller/peristaltic pumps 13 and 14, as will be explained in greater detail below. A supply power switch or mains switch 15 and a pilot light 16 are used to operate and monitor the device, respectively.

Figure 2:
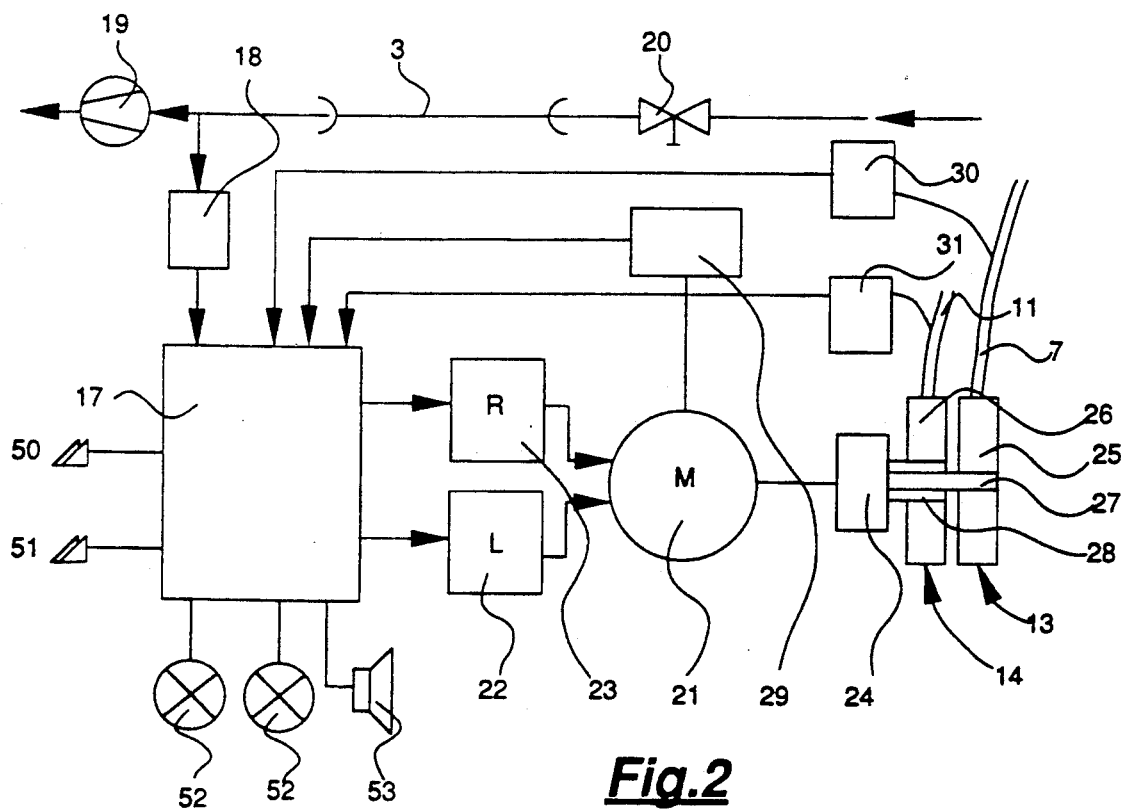
FIG. 2 is circuit diagram of the control device according to the invention.

FIG. 2 shows the control device 1 accommodated in the housing. This control device 1 comprises an evaluating electronic unit 17, to which the control line 3 is connected via a pressure sensor 18. A vacuum pump 19 and a control valve 20, which is part of the medical instrument 5, is inserted into the control line 3, as will be explained in greater detail on the basis of FIG. 3. A drive motor 21 for the peristaltic pumps 13 and 14 is connected to the evaluating electronic unit 17 via two motor power elements 22 and 23, of which element 22 is used for counterclockwise rotation and element 23 for clockwise rotation of the electric motor 21. The motor 21 is connected via a switching gear 24 to the two peristaltic pumps 13 and 14, whose rollers 25 and 26 are mounted on coaxial shafts 27 and 28. Each of the coaxial shafts 27 and 28 is mounted to the switching gear 24. The motor 21 is also provided with an actual value transducer 29 for the rotation speed, which is also connected to the evaluating electronic unit 17. The actual value transducer 29 permits the nominal value actual value comparison of the motor speed by means of the evaluating electronic unit 17 and consequently the nominal value-actual value comparison of the delivery capacities of the two peristaltic pump 13 and 14.

The evaluating electronic unit 17 is also connected to pressure sensors 30 and 31, which are associated with the irrigation line 7 and the aspiration line 11. The pressure sensors 30 and 31 enable the evaluating electronic unit 17 to control the device according to the desired irrigation and aspiration pressures.

FIG. 3 shows a schematic longitudinal section through the medical instrument 5. The medical instrument 5 comprises a handle 32 at one end and a double-lumen cannula needle 33 at the other end. The irrigation tube 34, which has a smaller diameter, is arranged inside the suction tube 35, which has a larger diameter. Correspondingly, the connection port 6 is connected to the irrigation tube 34 and the connection port 10 is connected to the suction tube 35. The irrigation line 7 is connected to the connection port 6 and the aspiration line 11 is connected to the connection port 10.

The connection port 4 for the control line 3 is provided between the connection ports 6 and 10 and the handle 32. The connection port 4 is provided with a suction opening 37 for control air via a needle valve 36. The needle valve 36 consists of a needle shaft 38 and a control needle 39, which engages in a valve opening 40. The needle shaft 38 is connected via a pin 41 to an outer sleeve 42, which can be set into a middle position by means of a locking device 43 and is continuously adjustable in both directions. The pumps 13 and 14 are thus continuously controllable and can be set in the neutral middle position.

FIG. 4 shows another embodiment of the cannula needle 3 of the medical instrument 5. A needle valve 44, whose valve needle 45 is adjustable to form different valve openings, is arranged at the outlet of the irrigation tube 33. The stream of irrigation fluid can thus be adjusted to form a spray cone, with which the gas filling in the abdomen can be rinsed to remove mist and vapor components during the use of a surgical laser.

Figure 5:
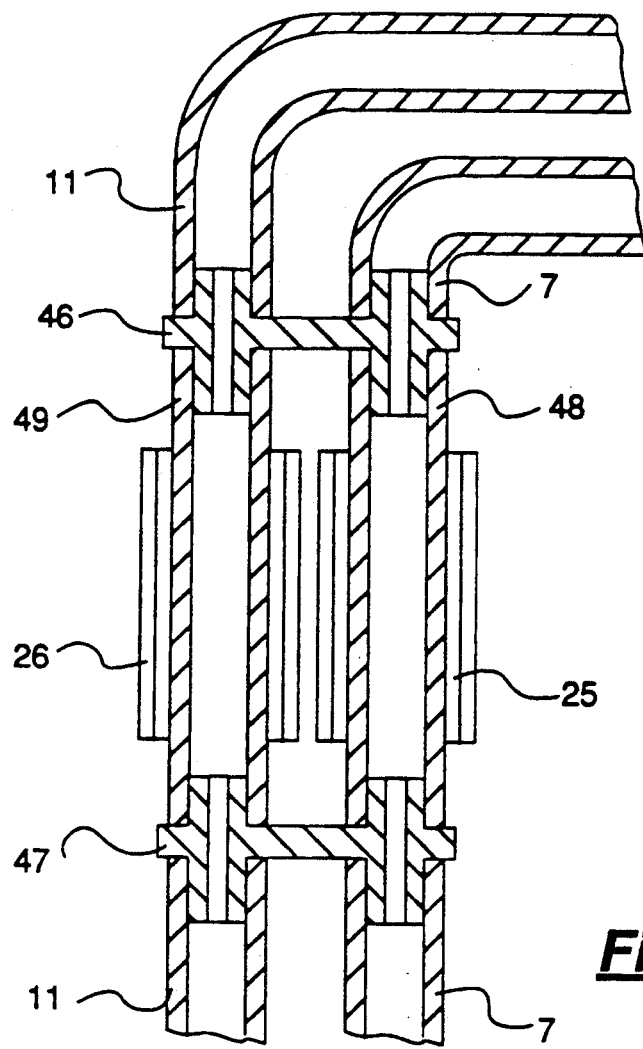
FIG. 5 is an enlarged sectional view through a set of tubings for two coaxially arranged peristaltic pumps; and, FIG. 6 is a top view of a simplified arrangement of the medical instrument according to the invention.

FIG. 5 shows a set of tubings for the two peristaltic pumps 13 and 14 The tubings are mounted in the switching gear 24 with shafts 27 and 28 which are arranged coaxially in each other. The irrigation line 7 and the aspiration line 11 are subdivided and connected by common tubing holders 46 and 47. The parts of the irrigation line 7 and the aspiration line 11 located between the tubing holders 46 and 47 are laid around the respective rollers 25 and 26 of the peristaltic pump 13 and 14. These have a common pressing bar.

The device according to the present invention operates as follows: After the control device 1 has been turned on, the vacuum set with the needle valve 36 of the medical instrument 5 is measured with the pressure sensor 18. The evaluating electronic unit 17 controls the drive motor either in a counterclockwise rotation direction 22 or in clockwise rotation direction 23. The direction of rotation depends on the vacuum input signal. This pressure signal is a voltage that is proportional to the vacuum from the pressure sensor 18 which is equipped with an amplifier. When this signal is in the middle range, the drive motor 21 is not energized, and neither irrigation nor aspiration takes place. Depending on the direction of rotation of the drive motor 21, the roller 25 or the roller 26 is operated for aspiration. During the operation of the roller 25 for irrigation, the irrigation line 7, designed as a tubing, delivers irrigation fluid from the supply reservoir 8 to tubing 48, which is laid around the roller 25 of the peristaltic pump 13. From here, the irrigation line 7 delivers the irrigation fluid to the irrigation tube 34 inside the medical instrument 5. When the pump roller 26 of the peristaltic pump 14 is operated for aspiration, the fluid to be drawn off is fed into the aspiration line 11 via the tube 35 of the medical instrument. The aspiration line 11, which is also designed as a length of tubing, will then deliver the fluid to be drawn off to the pump tubing 49 laid around the roller 26. By this arrangement this fluid is fed to the collection reservoir 12 via the aspiration line 11. The supply reservoir 8 and the collection reservoir 12 may also be designed as bags. The collection reservoir 12 can thus be disposed of together with its contents. The two tubing holders 46 and 47 are designed such that these cannot be placed elsewhere at all because of their form-fitting relationship to the two peristaltic pumps 13 and 14. Thus, the complete set of tubings can be designed, in a very advantageous manner, as a disposable set. The operating personnel is thereby exposed to a reduced risk of infection due to the fact that neither a collection reservoir nor a collection bottle with overflow protection device needs to be washed. Due to the fact that the suction capacity of the roller pump 14 can be changed rather rapidly, in contrast to the evacuated collection bottle, it is possible to draw off very small pools of liquid without the medical instrument 5 being sucked firmly against the tissue. The switching gear 24 permits a compact and light-weight design of the device to be realized.

In the simplest case, the medical instrument 5, which is introduced into the body cavity by means of a trocar, may be a thin-walled tube with an external diameter of approx. 5 mm. The connection ports 6 and 10 for the irrigation line 7 and the aspiration line 11 are arranged between the proximal end and the handle 32 of the medical instrument 5. Due to the fact that the tubing lines 48 and 49 of the irrigation line 7 and of the aspiration line 11 are closed by the peristaltic pumps 13 and 14, which are designed as roller pumps, no valve is needed on the device. The cannula needle 33 serves as an irrigation tube and a suction tube at the same time.

The design of the distal end of the medical instrument 5, which is shown in FIG. 4, provides that the irrigation tube 34, being the inner tube of the instrument 5, has a nozzle outlet, which is provided with the needle valve 44. This enables the surgeon to produce a jet with higher or lower energy, depending on the output of the associated roller pump 13, without having to use an unnecessarily large amount of irrigation fluid. The residual cross section of the cannula needle 33 is used for aspiration as a suction tube 35.

When the outlet nozzle of the needle valve 44 is moved into one end of the adjustable nozzle on the instrument 5, a coherent stream of irrigation fluid, is generated, and a rather homogeneous spray cone with a cone angle of at least 90°, is generated when moved into another end. Thus it is possible to rinse off clots from the tissue, on one hand, and also to wash mists and vapors from the gas bubble in the abdomen during the use of a surgical laser, on the other hand. This variation is made possible by changing the axial position of the valve cone relative to the irrigation tube 34. Physiologically safe additives to the irrigation fluid can enhance the washing out of the laser residues. Generating a homogeneous spray cone requires a higher dynamic pressure of approx. .1 bar in front of the outlet nozzle in the front of the needle valve 44, which pressure is generated most simply with the roller pump To control the aspiration and irrigation process, the medical instrument 5 has the connection port 4, which opens into the needle valve 36, which can be positioned in either direction around a middle position by means of a displaceable outer sleeve 42. Additional possibilities for controlling the peristaltic pump combination with pedals for counterclockwise and clockwise rotation of the motor 21 are given by the pedals 50 and 51 connected to the control device 17. Furthermore, the control device 17 is associated with optical and acoustic signal-generating devices, which signal the operating conditions of the device.

Figure 6:
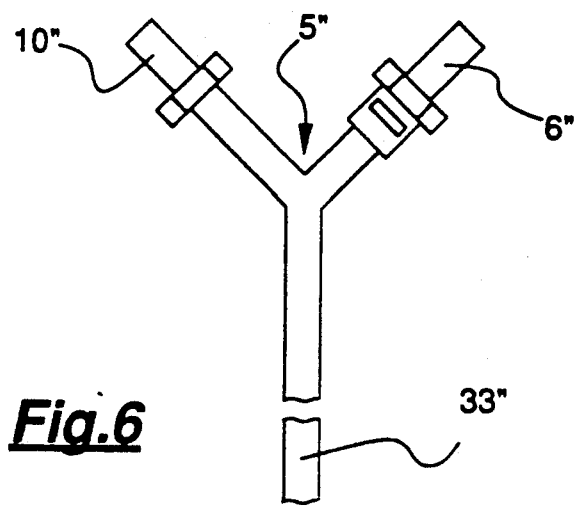

FIG. 6 shows a simplified embodiment of the medical instrument 5″, in which the connection ports 6″ and 10″ open into a common cannula needle 33″.

While specific embodiments of the invention have been shown and described in detail to illustrate the application of the principles of the invention, it will be understood that the invention may be embodied otherwise without departing from such principles.

What is claimed is:

1. A device for irrigation of, and aspiration from, a body cavity, the device comprising:
    a delivery pump formed as a peristaltic/roller pump;
    a suction pump formed as a peristaltic/roller pump;
    a delivery pump shaft and a suction pump shaft, said delivery pump shaft and said suction pump shaft being arranged coaxially;
    a first tubing line connected to said delivery pump and leading to the body cavity;
    a second tubing line connected to said suction pump and leading to the body cavity;
    switching means connected to said pump shafts and control means connected to said switching means for controlling the irrigation and aspiration of the body cavity.

2. A device according to claim 1, further comprising holding elements, which hold said first and second tubing lines inside with respect to said delivery and suction pumps in a form-fit relationship relative to one another and include connecting nozzles of different diameters, provided for the tubing lines used for irrigation and aspiration, such that mix-up of the tubing lines is not possible.

3. A device in accordance with claim 1, wherein:
    said delivery and suction pumps have a common pressing bar.

4. A device in accordance with claim 1, wherein:
    said delivery pump and said suction pump are driven by a common motor.

5. A device or irrigation of an aspiration from a body cavity the device comprising:
    a delivery pump formed as a peristaltic/roller pump;
    a suction pump formed as a peristaltic/roller pump;
    a delivery pump shaft and a suction pump shaft, said delivery pump shaft and said suction pump shaft being arranged coaxially;
    a first tubing line connected to said delivery pump and leading to the body cavity;
    a second tubing line connected to said suction pump and leading to the body cavity;
    switching means connecting a common motor to said pump shafts;
    control means connected to said delivery pump and said suction pump for controlling the irrigation and aspiration of the body cavity, said control means having a control line, said control line having a control line regulator means for regulating gas pressure in said control line, said control means controlling the irrigation and aspiration of the body cavity based on said gas pressure in said control line.

6. A device according to claim 5, wherein said control means comprises a vacuum pump connected to said control line.

7. A device according to claim 6 wherein said control line regulator means is arranged in the area of a handle of a medical instrument and said first and second tubing lines connected to said delivery and suction pumps can be connected to two connection ports of said medical instrument, said medical instrument being formed with a hollow shaft.

8. A device accordance to claim 7, further comprising a needle valve, having a value needle which is adjustable to form different valve openings, said valve needle being arranged at an outlet of said irrigation tube, inside the medical instrument.

9. A device according to claim 5 wherein said control line regulator means is arranged in the area of a handle or a medical instrument and said first and second tubing lines connected to said delivery and suction pumps can be connected to two connection ports of said medical instrument, said medical instrument being formed with a hollow shaft.

10. A device according to claim 9, wherein said medical instrument has a double lumen with a suction tube and an irrigation tube, said irrigation tube is provided with a smaller diameter than said suction tube and is arranged inside said suction tube.

11. A device according to claim 10, wherein said control line regulator means has a connection port for said control line and inlet openings for a gaseous control medium, and a needle valve is provided which is actuated by means of an outer sleeve which is provided between the inlet openings and the connection port.

12. A device according to claim 9, wherein said control line regulator means has a connection port for said control line and inlet openings for a gaseous control medium, and a needle valve is provided which is actuated by means of an outer sleeve which is provided between the inlet openings and the connection port.

13. A device according to claim 12, wherein said outer sleeve is adjustable by means of a locking device to lock positions associated with different sleeve openings of the needle valve.

* * * * *